(12) United States Patent
Malewicz

(10) Patent No.: US 7,393,358 B2
(45) Date of Patent: Jul. 1, 2008

(54) STENT DELIVERY SYSTEM

(75) Inventor: Andrzej Malewicz, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 452 days.

(21) Appl. No.: 10/920,082

(22) Filed: Aug. 17, 2004

(65) Prior Publication Data

US 2006/0041302 A1    Feb. 23, 2006

(51) Int. Cl.
*A61F 2/06* (2006.01)
(52) U.S. Cl. ............... 623/1.11; 623/1.12; 623/1.42; 606/108
(58) Field of Classification Search ............... 623/1.11, 623/1.12, 1.42; 606/108
See application file for complete search history.

(56) References Cited

U.S. PATENT DOCUMENTS

| | | | | |
|---|---|---|---|---|
| 4,732,152 A * | 3/1988 | Wallsten et al. | ............ | 623/1.11 |
| 5,662,703 A * | 9/1997 | Yurek et al. | ................ | 623/1.12 |
| 5,681,345 A | 10/1997 | Euteneuer | ................... | 62/1.11 |
| 5,788,707 A | 8/1998 | Del Toro et al. | ........... | 623/1.11 |
| 6,066,155 A | 5/2000 | Amann et al. | ............... | 606/192 |
| 6,096,045 A | 8/2000 | Del Toro et al. | ............ | 606/108 |
| 6,221,097 B1 | 4/2001 | Wang et al. | ................. | 623/1.11 |
| 6,331,186 B1 | 12/2001 | Wang et al. | ................. | 623/1.11 |
| 6,342,066 B1 | 1/2002 | Toro et al. | .................. | 623/1.11 |
| 6,350,277 B1 | 2/2002 | Kocur | ....................... | 623/1.11 |
| 6,443,880 B2 | 9/2002 | Blais et al. | .................... | 492/16 |
| 6,478,814 B2 | 11/2002 | Wang et al. | ................. | 623/1.12 |
| 6,755,855 B2 * | 6/2004 | Yurek et al. | ................ | 623/1.12 |
| 6,942,682 B2 | 9/2005 | Vrba et al. | ................... | 606/198 |
| 2004/0143272 A1 | 7/2004 | Cully et al. | .................. | 606/108 |
| 2004/0143315 A1 | 7/2004 | Bruun et al. | ............... | 623/1.11 |
| 2004/0167603 A1 * | 8/2004 | Jackson et al. | ............. | 623/1.12 |
| 2004/0199239 A1 * | 10/2004 | Austin et al. | ............... | 623/1.11 |
| 2005/0033402 A1 | 2/2005 | Cully et al. | ................. | 623/1.11 |
| 2005/0038495 A1 | 2/2005 | Greenan | .................... | 623/1.11 |
| 2006/0030923 A1 * | 2/2006 | Gunderson | ................. | 623/1.11 |

FOREIGN PATENT DOCUMENTS

| | | |
|---|---|---|
| EP | 0 537 985 | 4/1993 |
| WO | WO 96/32078 | 10/1996 |
| WO | WO 01/78627 | 10/2001 |
| WO | WO 02/38084 | 5/2002 |

\* cited by examiner

*Primary Examiner*—Kevin Truong
*Assistant Examiner*—Katherine M Dowe
(74) *Attorney, Agent, or Firm*—Vidas, Arrett, & Steinkraus

(57) ABSTRACT

A medical device comprises a catheter, a retractable sheath, and a rolling membrane. The catheter includes a catheter shaft about which a stent in a reduced diameter configuration may be disposed. A stent retaining region of the sheath is disposed about the stent to retain the stent in the reduced diameter state prior to delivery. The rolling membrane is engaged to a portion of the sheath at an engagement region. The rolling membrane is positioned between the catheter shaft and the sheath and prior to retraction of the sheath the rolling membrane is disposed about at least a proximal section of the stent and is rollingly retracted therefrom when the sheath is retracted to deliver the stent.

28 Claims, 6 Drawing Sheets

STENT DELIVERY SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates to catheters and catheter assemblies for use in medical procedures. More specifically, this invention relates to a stent delivery catheter system, such as the kind used in percutaneous transluminal coronary angioplasty (PTCA) procedures, for the delivery of a stent into a body lumen.

2. Description of the Related Art

Percutaneous transluminal coronary angioplasty (PTCA) is a procedure which is well established for the treatment of blockages, lesions, stenosis, thrombus, etc. present in body lumens such as the coronary arteries and/or other vessels.

A widely used form of percutaneous coronary angioplasty makes use of a dilatation balloon catheter which is introduced into and advanced through a lumen or body vessel until the distal end thereof is at a desired location in the vasculature. Once in position across a afflicted site, the expandable portion of the catheter, or balloon, is inflated to a predetermined size with a fluid at relatively high pressures. By doing so the vessel is dilated, thereby radially compressing the atherosclerotic plaque of any lesion present against the inside of the artery wall, and/or otherwise treating the afflicted area of the vessel. The balloon is then deflated to a small profile so that the dilatation catheter may be withdrawn from the patient's vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, such as a stent, inside the artery at the lesion.

Stents, grafts, stent-grafts, vena cava filters, vascular implants, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, such as a nitinol shape memory stent, mechanically expandable, such as a balloon expandable stent, or hybrid expandable.

Prior to delivery a stent or stents may be retained on a portion of the delivery catheter by crimping the stent onto the catheter, retaining the stent in a reduced state about the catheter with a removable sheath, sleeve, sock or other member or members, or by any of a variety of retaining mechanisms or methods. Some examples of stent retaining mechanisms are described in U.S. Pat. No. 5,681,345; U.S. Pat. No. 5,788,707; U.S. Pat. No. 6,066,155; U.S. Pat. No. 6,096,045; U.S. Pat. No. 6,221,097; U.S. Pat. No. 6,331,186; U.S. Pat. No. 6,342,066; U.S. Pat. No. 6,350,277; U.S. Pat. No. 6,443,880; U.S. Pat. No. 6,478,814 and U.S. patent application Ser. No. 09/664,268 entitled Rolling Socks and filed Sep. 18, 2000.

The present invention provides catheter assemblies with a variety of embodiments and features which improve stent retention and deployment characteristics.

All US patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to a variety of embodiments. For example, in at least one embodiment the invention is directed to a stent delivery catheter having an inner membrane and an outer pull-back sheath wherein prior to delivery of the stent the inner membrane overlaps only a proximal portion of the stent and the outer sheath extends over substantially the entire length of the stent.

In at least one embodiment the outer sheath has a greater hoop strength than the than the inner membrane. In some embodiments the inner membrane has a greater flexibility than that of the sheath. The membrane is also characterized as being constructed and/or coated with a material that is substantially non-blocking relative to a drug or other therapeutic agent placed on the stent.

In at least one embodiment the membrane is a rolling membrane. Prior to delivery of the stent, the membrane may be characterized as being disposed about a proximal portion of the stent in a folded over configuration such that a proximal section of the membrane is folded over a distal section of the membrane and a proximal end of the membrane is engaged to a proximal portion of the outer sheath. The membrane may alternatively be characterized such that when the membrane is extended the inner layer forms a proximal section and the outer layer forms a distal section. Upon retraction of the outer sheath from about the stent, the membrane is rollingly retracted from the stent as the distal section of the membrane is drawn proximally over the proximal section until the membrane is fully retracted from the stent. In at least one embodiment at least a portion of one or more of the proximal section and distal section of the membrane is coated with a lubricious substance.

In some embodiments the membrane may be disposed about any or all portions of the stent prior to retraction. In at least one embodiment, prior to the retraction of the sheath, the membrane is disposed about approximately half the length of the stent.

In some embodiments the membrane is a single layer membrane which in the un-retracted state comprises the folded over configuration previously described, and in the fully retracted state is unfolded to form a single layer. In at least one embodiment however, the membrane comprises a continuous double layer membrane which rollingly retracts from the stent during pull-back retraction of the sheath but which retains the double layer configuration prior to, during and after retraction from about the stent.

Where the membrane comprises a continuous double layer membrane, a portion of one layer of the membrane is engaged to a distal or mid-distal portion of the sheath in order to facilitate complete withdraw of the inner membrane from the stent during retraction of the outer sheath. In at least one embodiment the continuous double layer membrane defines a chamber or space. In some embodiments the chamber includes a lubricious substance therein.

These and other embodiments which characterize the invention are pointed out with particularity in the claims annexed hereto and forming a part hereof However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
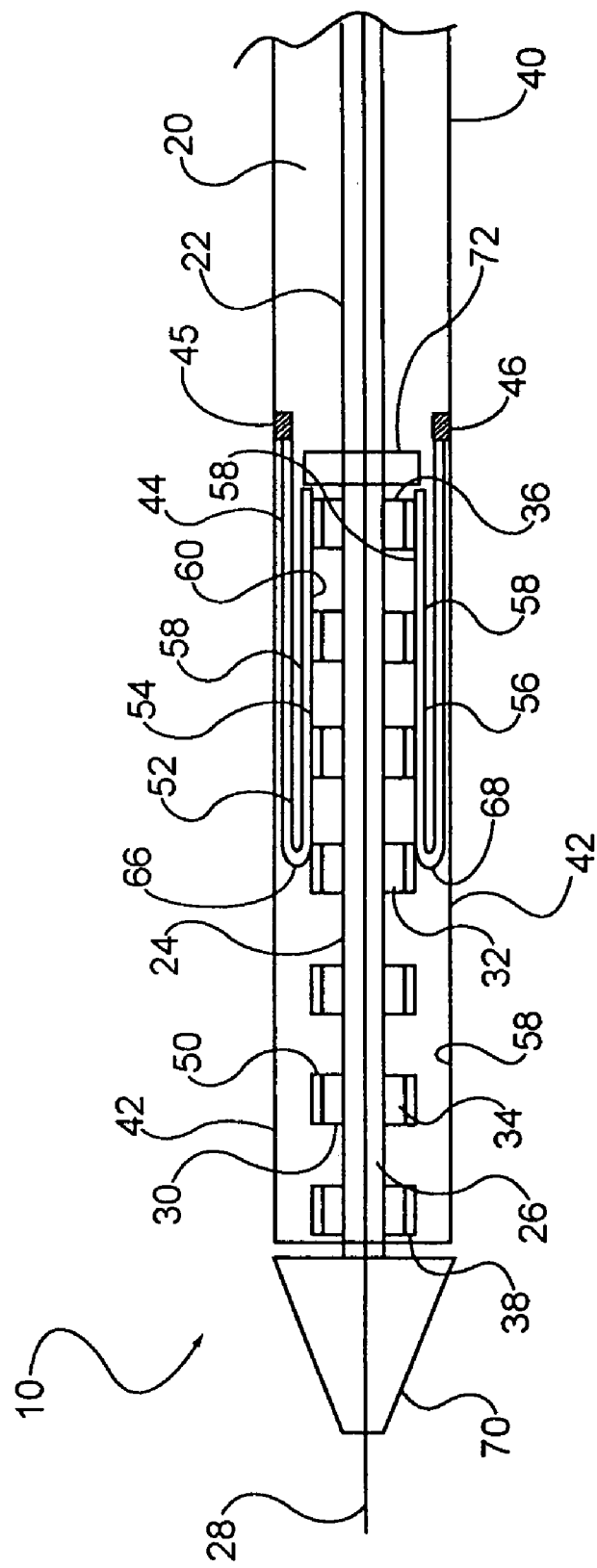
FIG. 1 is a cross-sectional side view of an embodiment of the invention having a single layer rolling membrane.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
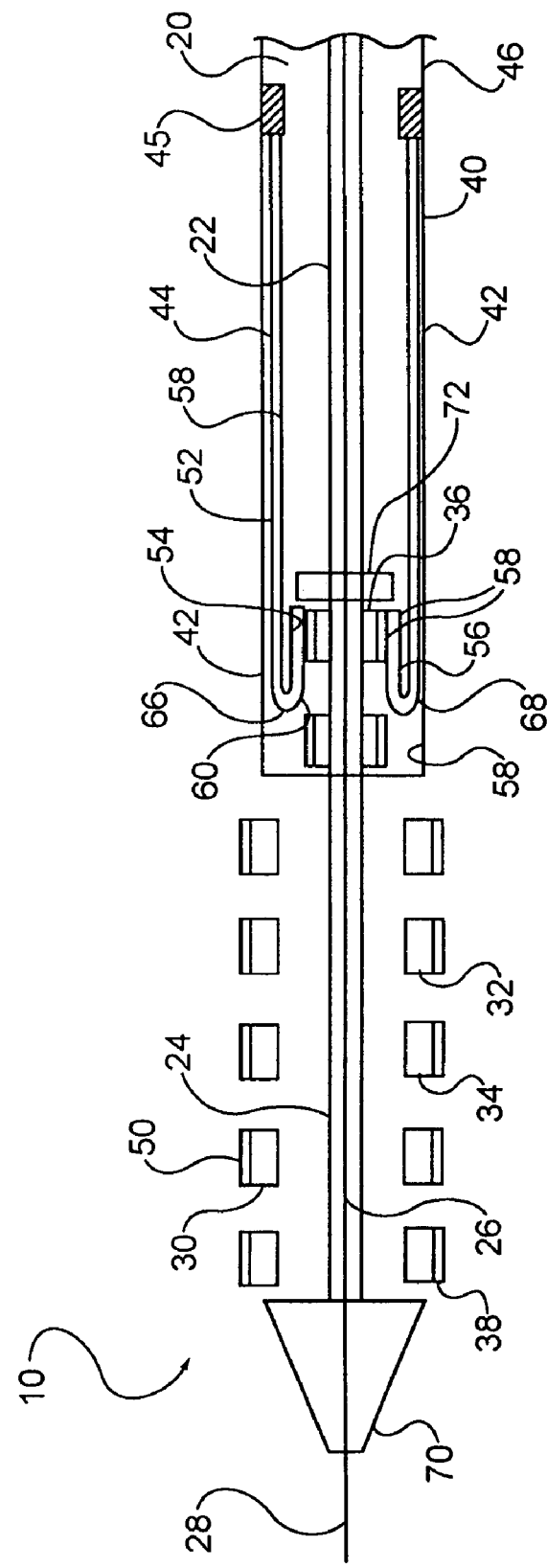
FIG. 2 is a cross-sectional side view of the embodiment depicted in FIG. 1 shown during retraction of the membrane and delivery of the stent.
Figure 3:
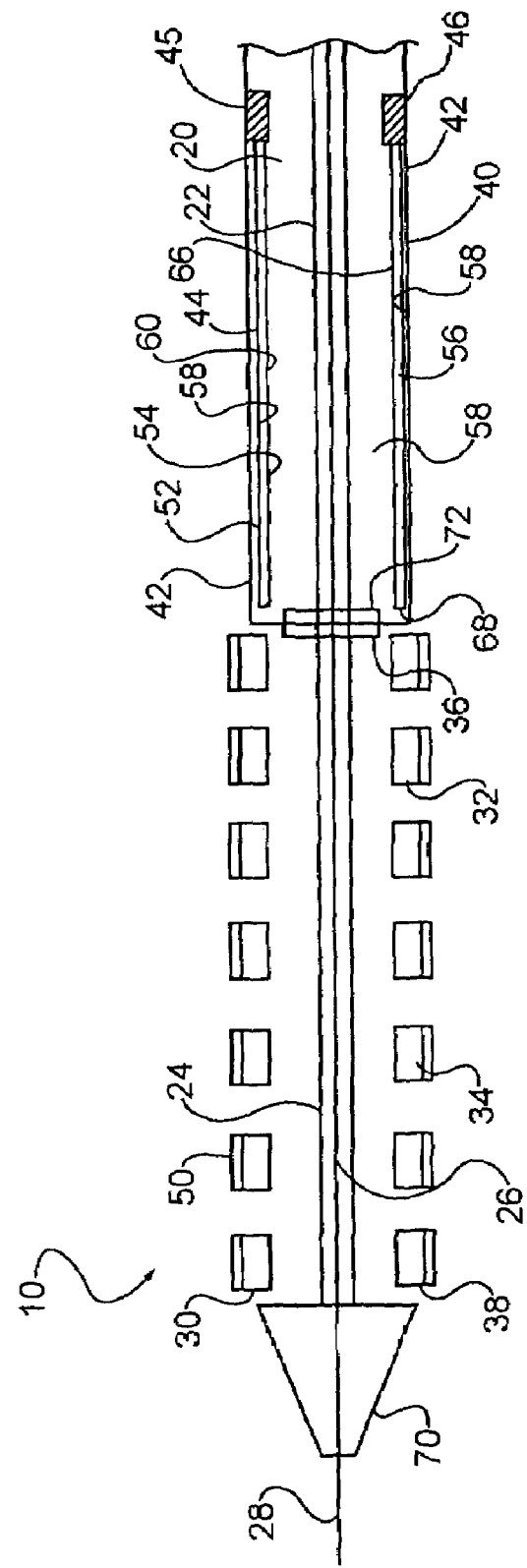
FIG. 3 is a cross-sectional side view of the embodiment depicted in FIG. 1 shown with the membrane fully retracted from the stent.

In at least one embodiment, an example of which is shown in FIGS. 1-3, a delivery system 10, is depicted which includes a catheter 20 which is configured to deliver a stent 30, which in at least one embodiment is a self-expanding stent.

Catheter 20 includes a catheter shaft 22, a portion of which defines a stent receiving region 24. Catheter shaft 22 may further define a guidewire lumen 26 through which a guidewire 28 may be passed in order to advance the catheter to a predetermined position in a body lumen or vessel. Alternatively, the shaft 22 may be configured as a fixed-wire catheter.

As shown in FIG. 1, a stent 30 may be a self-expanding stent which is disposed about the stent receiving region 24 of the catheter shaft 22. In some embodiments the stent may be at least partially constructed from one or more of the following shape memory materials: nitinol, shape-memory polymer(s), etc., but may include other material or materials as well. In some embodiments the stent includes one or more areas, bands, coatings, members etc that is (are) detectable by imaging modalities such as X-Ray, MRI or ultrasound. In some embodiments at least a portion of the stent 30 is at least partially radiopaque.

In some embodiments the stent 30 may include one or more therapeutic and/or lubricious coatings 50 applied thereto.

A therapeutic agent may be included with the stent. In some embodiments the agent is placed on the stent in the form of a coating 50. In at least one embodiment the coating 50 includes at least one therapeutic agent and at least one polymer agent.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic includes cellular material, the cellular material may include but is not limited to: cells of human origin and/or non-human origin as well as their respective components and/or derivatives thereof Where the therapeutic agent includes a polymer agent, the agent may be a polystyrene-polyisobutylene-polystyrene triblock copolymer (SIBS), polyethylene oxide, silicone rubber and/or any other suitable substrate.

In the various embodiments described herein the stent 30 is preferably configured to be at least partially self-expanding or have self-expanding characteristics. As used herein the term "self-expanding" refers to the tendency of the stent to return to a predetermined diameter when unrestrained from the catheter, such as in the manner depicted in FIGS. 1-3. In the present embodiment when the stent is disposed about the stent receiving region 24 of the catheter shaft 22, the stent is restrained in its reduced diameter or pre-delivery configuration by retractable sheath 40 which is disposed about the entire length of the stent 30 prior to delivery.

The sheath 40 includes a stent retaining region 42, which refers to that region of the sheath 40 which is disposed about the stent 30 prior to delivery. Engaged to a portion of the stent retaining region 42 is an inner sleeve or membrane 44. When the stent 30 is delivered the sheath 40 and membrane 44 are retracted from about the stent in the manner illustrated in FIGS. 2-3.

In some embodiments, particularly where the stent 30 employs one or more therapeutic agents coatings 50 thereon, it is necessary to take into account the need to maintain the coating's integrity when being deployed by withdrawal of the sheath 40.

In the case of a drug coated stent, the interaction of the interaction of forces between the proximal portion of the stent and a traditional sheath may affect the integrity of the coating as it is rubbed or otherwise disturbed by the sheath as the stent pushes against the sheath as it is being retracted.

In the various embodiments of the present invention, a passively rolling membrane 44 is disposed about at least a portion of the stent prior to delivery.

In the embodiments depicted in FIGS. 1-3 the membrane 44 is a single layer membrane folded over upon itself prior to delivery. In the folded over configuration an outer fold 52 of the membrane 44 is positioned between the sheath 40 and an inner fold 54, and the inner fold 54 extends from the outer fold 52 and extends thereunder against the at least a portion of the stent 30. A proximal end region 45 of the membrane comprises an engagement region 46 wherein the membrane 44 is engaged to the sheath 40. When the sheath 40 is retracted, the membrane 44 is pulled back off of the stent 30 as the outer membrane 52 rolls proximally on top of the inner fold 54 proximally until the entire membrane 44 is rolled off of the stent 30 such as is depicted in FIGS. 1-3.

The rolling action of the membrane 44, such as is depicted during withdrawal of the sheath 40 in FIGS. 2 and 3, reduces and/or eliminates the sliding interaction between the sheath 44 and the proximal region 32 of the stent 30. Because the membrane is originally positioned over the proximal region 32 of the stent 30 upon full retraction of the sheath 40 the membrane does not roll out distally beyond the distal end of the sheath 40.

Figure 4:
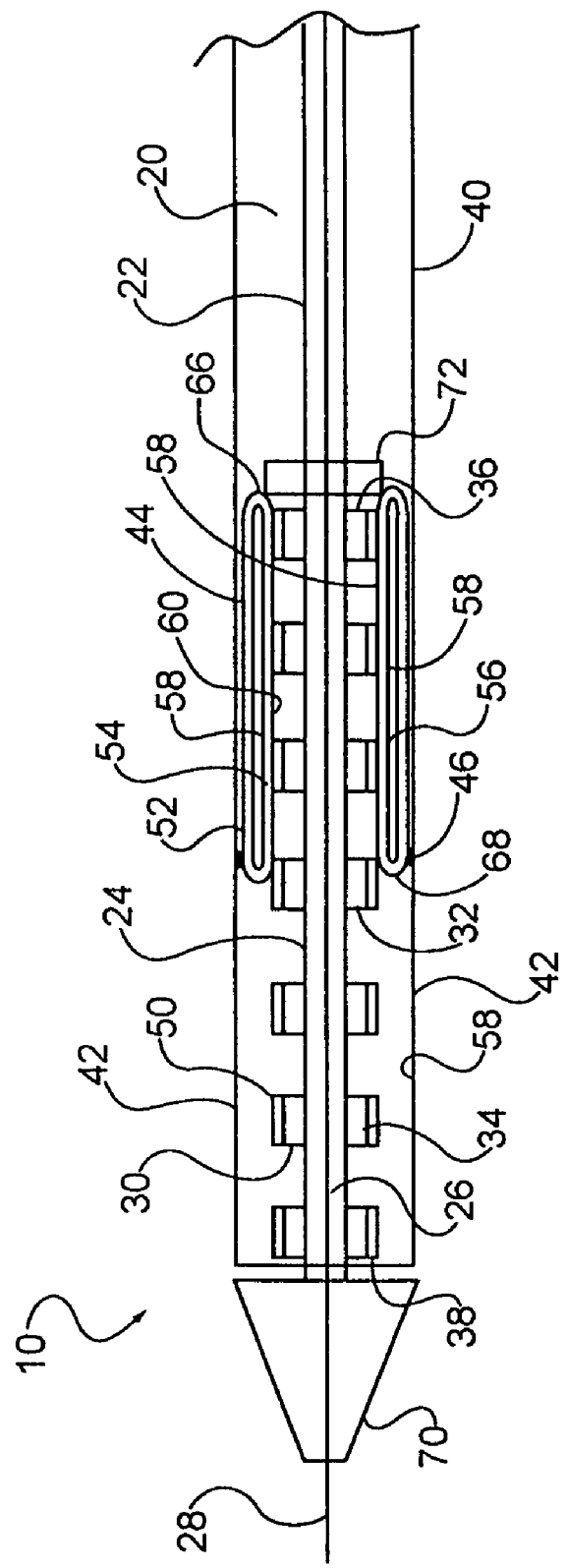
FIG. 4 is a cross-sectional side view of the embodiment shown in FIG. 1 wherein the membrane is a double layer rolling sheath.
Figure 5:
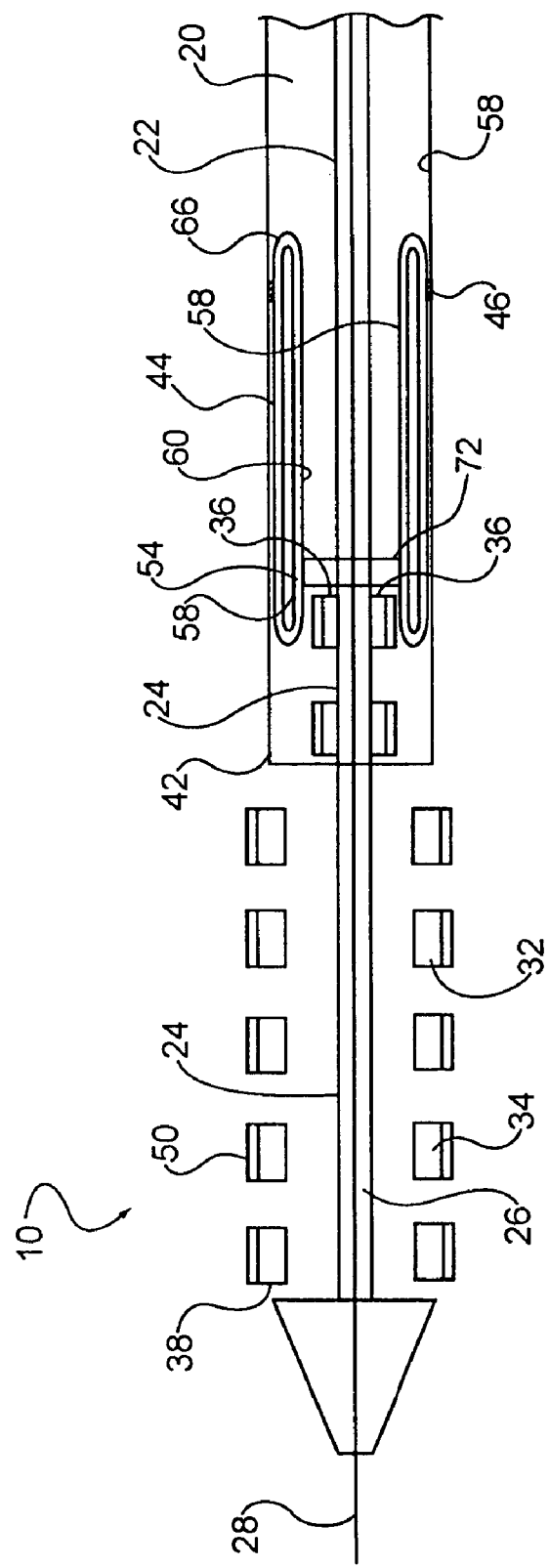
FIG. 5 is a cross-sectional side view of the embodiment depicted in FIG. 4 shown during retraction of the membrane and delivery of the stent.
Figure 6:
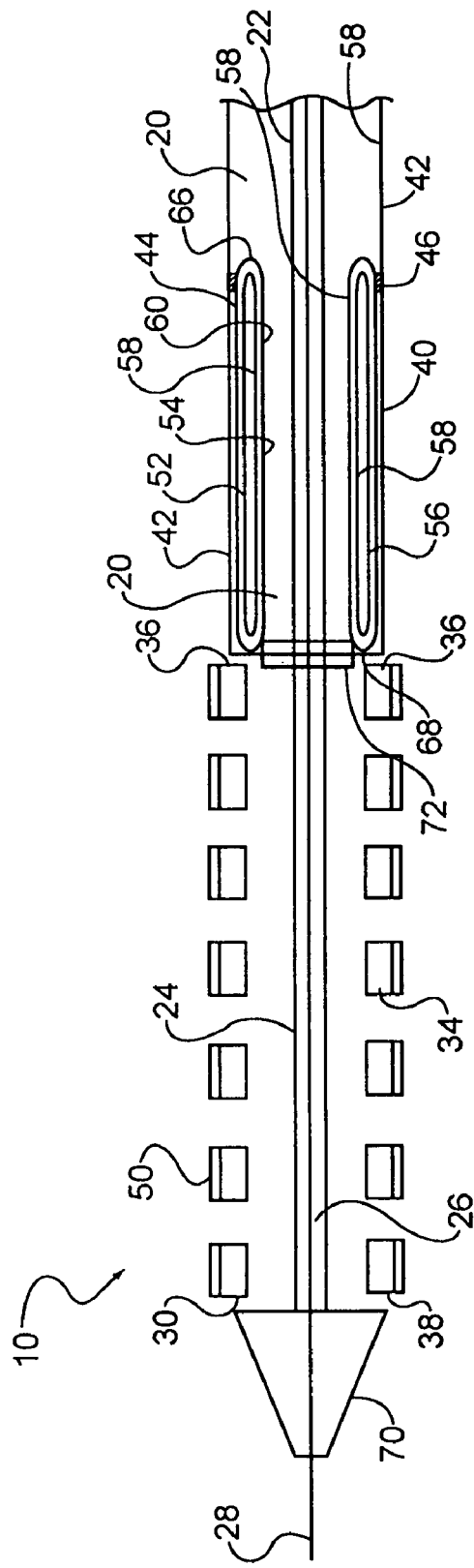
FIG. 6 is a cross-sectional side view of the embodiment depicted in FIG. 4 shown with the membrane fully retracted from the stent.

As is shown in the various figures, the membrane 44 is engaged to the sheath 40 at an engagement region 46. In the case of the single layer folded over membrane shown in FIGS. 1-3 the proximal end region 45 of the membrane is engaged to the sheath 40 at an engagement region 46. In the case of a continuous layer membrane, such as is shown in FIGS. 4-6, the engagement region 46 is positioned at a distal region 68 of the membrane prior to delivery, but following full retraction of the membrane 44 off of the stent 30 the engagement region is in effect shifted to a proximal region 66, such as is depicted in FIG. 6.

The engagement region 46 may be any form of engagement between the membrane 44 and sheath 40. The engagement region may be a series of engagement points circumferentially distributed about an interface between the sheath 40 and membrane 44. Alternatively, the engagement region may be in the form of a collar shaped interface or other configuration. The engagement between the sheath 40 and membrane 44 may be by welding, chemical adhesive, physical engagement or other form of engagement.

Because the sheath 40, and particularly the distal portion or stent retaining region 42 of the sheath, is configured to retain the stent 30 in its reduced or pre-delivery diameter, the stent retaining region 42 of the sheath 40 is constructed to have sufficient hoop strength to prevent the stent from expanding off of the stent receiving region 24 until the sheath 40 is retracted. At least the stent retaining region 42 of the sheath 40 may be constructed from one or more of the materials including but not limited to: various formulations of polyurethane, polytetrafluoroethylene ((PTFE) including ePTFE and siliconized PTFE), high density polyethylene (HDPE), polyamide, polyimide, etc.

While the stent retaining region 42 of the sheath 40 is typically constructed to have greater hoop strength than the membrane 44, the sheath may be less flexible than the membrane 44 as well. The membrane 44 may be at least partially constructed of one or more of a variety of flexible materials such as including but not limited to: polyester, polyamide, polyethylene terephalate (PET), crosslinked polyethylene, polyurethane, plasticized PVC (polyvinylchloride), PTFE, nylon, polyether block amides (PEBAX), silicone, POC, polyether, etc. In at least one embodiment the membrane 44 is at least partially constructed from those materials from which medical balloons are known to be manufactured from.

As indicated above the stent 30 may be characterized as having a proximal portion 32 as well as a distal portion 34. As used herein a proximal portion 32 of the stent may refer to about 50 percent of the length of the stent as measured from the proximal edge 36, however in at least one embodiment the proximal portion 32 is at least about 30 percent of the length of the stent to about 70 percent of the length of the stent as measured from the proximal edge 36 of the stent 30.

In some embodiments the membrane 44 is inter-disposed between the sheath 40 and the entire length of the stent 30 prior to retraction of the sheath.

During delivery of the stout 30 the sheath 40 is retracted proximally from the stent in the manner depicted in FIG. 2. As a result of the engagement between the membrane 44 and the sheath 40 at the engagement region 46, during retraction the outer fold 52 of the membrane 44 will roll proxinially on top of the inner fold 54 until the entire membrane 44 is rolled off of the stent 30 as the outer fold 52 rolls completely off of the inner fold 54 as depicted in FIG. 3. To encourage the rolling action of the folds 52 and 54, in some embodiments the inside surface 56 of the membrane 44, as defined by the interface between the outer fold 52 and the inner fold 54, may be coated with a lubricious coating 58. Coating 58 may be any sort of biocompatible material such as is described in U.S. Pat. No. 5,693,034, the entire content of which is incorporated herein by reference; and/or other lubricious materials.

In some embodiments, coating 58 may also be applied to at least a portion of the exterior surface 60 of the membrane 44. In at least one embodiment coating 58 is applied to the exterior surface 60 of the inner fold 54 where the membrane 44 overlays the proximal region 32 of the stent 30 prior to delivery. In some embodiments the coating 58 is applied to at least a portion of the interior surface 64 of the stent retaining region 42 of the sheath 40.

As indicated above, in the embodiments shown in FIGS. 1-3 the membrane 44 is a single layer membrane which is rolled upon itself to form outer fold 52 and inner fold 54 prior to delivery of the stent 30. An end 45 of the membrane 44 is engaged to the sheath 40 at the engagement region 46.

In at least one embodiment, an example of which is depicted in FIGS. 4-6, the membrane 44 is a continuous double walled tube which rolls off of the stent 30 from an engagement region 46 that is initially at the distal end 68 of the membrane but during retraction of the sheath 40 transitions to the proximal end 66 of the membrane 44 as a consequence of the rolling action of the membrane during retraction as depicted in FIGS. 5 and 6. Thus, the layers 52 and 54 of the membrane 44 remain in continuous overlapping engagement before, during and after delivery of the stent 30.

In some embodiments the inside surface 56 of the of the membrane membrane 44 may be provided with coating 58.

In the various embodiments shown in and described herein the catheter 20 may employ various features to maintain the position of the stent 30 on the stent receiving region 24 prior to deliver and/or during retraction of the sheath 40. For example a catheter tip or other member 70 may act to bias the distal edge 38 of the stent 30 prior to delivery. The member 70 may have a diameter sufficiently greater than the diameter of the stent in the reduced state, thereby preventing the stent from being inadvertently displaced in the distal direction.

In some embodiments a hub, flange, protrusion(s), marker or other member 72 may be positioned proximally adjacent to the stent receiving region 24. Member 72 may also be provided with a diameter sufficiently greater than the diameter of the stent in the reduced state, to thereby prevent the stent from being inadvertently displaced in the proximal direction. Alternatively, the stent 30 may be crimped directly onto one or more of the members 70 and/or 72, and/or the catheter 20 may be provided any of the variety of stent retaining mechanisms that are known.

Members 70 and/or 72 may be configured to be detectable by imaging modalities such as X-Ray, MRI or ultrasound. In some embodiments at least a portion of one or both members is at least partially radiopaque.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A medical device comprising:
   a catheter, the catheter having a catheter shaft, a portion of the catheter shaft defining a stent receiving region;
   a sheath, a portion of the sheath defining a stent retaining region, the stent retaining region being disposed about the catheter shaft and being longitudinally moveable relative thereto, the retaining region being moveable between a fully extended position and a fully retracted position, in the fully extended position the retaining region being disposed about an entire length the stent receiving region, in the fully retracted position the sheath being removed from the stent receiving region;
   a stent, the stent being expandable from a reduced state to an expanded state, wherein the stent has a proximal edge, a distal edge and a length measured from between the proximal edge and distal edge, a proximal section of the stent defining about a half of the length of the stent as measured from the proximal edge, in the reduced state the stent having a diameter less than the diameter in the expanded state, when the sheath is in the fully extended position the stent is in the reduced state disposed about the stent receiving region; and
   a rolling membrane, the rolling membrane comprising an inner fold and an outer fold, a portion of the rolling membrane being engaged to a portion of the sheath at an engagement region, the rolling membrane being positioned between the catheter shaft and the sheath, in the fully extended position the inner fold surrounding only the proximal section of the stent, in the fully retracted position the inner fold being removed from about the proximal section of the stent.

2. The medical device of claim 1 wherein the rolling membrane comprises a proximal end and a distal end.

3. The medical device of claim 2 wherein the rolling membrane is defined by a single layer of membrane material.

4. The medical device of claim 3 wherein at least the proximal end of the rolling membrane is engaged to the portion of the sheath at the engagement region, the engagement region being positioned proximal of the proximal edge of the stent.

5. The medical device of claim 4 wherein in the extended position the single layer is folded over itself to form the inner fold and the outer fold at least partially radially adjacent one another, the outer fold extending distally from the engagement region over the proximal section of the stent, the inner fold extending proximally from the outer fold to the proximal edge of the stent.

6. The medical device of claim 5 wherein in the retracted position the single layer is unfolded, wherein the inner fold and the outer fold are not radially adjacent one another.

7. The medical device of claim 2 wherein the inner fold and the outer fold define a continuous double layer of membrane material.

8. The medical device of claim 7 wherein in the extended position the inner fold and the outer fold extend proximally from the engagement area over the proximal section of the stent.

9. The medical device of claim 8 wherein in the retracted position the inner fold and the outer fold extend distally from the engagement area and are retracted from about the stent.

10. The medical device of claim 1 wherein at least a portion of the rolling membrane includes a lubricious coating applied thereto.

11. The medical device of claim 10 wherein the rolling membrane has an inner surface and an outer surface, the lubricious coating being applied to at least a portion of at least one of the inner surface and outer surface of the rolling membrane.

12. The medical device of claim 1 further comprising a stent securing member, the stent securing member being engaged to the catheter shaft and being positioned immediately adjacent the stent receiving region.

13. The medical device of claim 12 wherein in the reduced state the stent is engaged to the stent securing member.

14. The medical device of claim 12 wherein the stent securing member comprises a proximal stent securing member and a distal stent securing member, the proximal stent securing member being positioned immediately adjacent a proximal end of the stent receiving region and the distal stent securing member being positioned immediately adjacent a distal end of the stent receiving region.

15. The medical device of claim 12 wherein the stent securing member is at least partially radiopaque.

16. The medical device of claim 12 wherein the stent securing member is configured to be detectable by at least one of the following detection modalities: X-Ray, MRI, ultrasound, and any combination thereof.

17. The medical device of claim 1 wherein the sheath is at least partially constructed of at least one material of the group consisting of: polyurethane, polytetrafluoroethylene, high density polyethylene, polyamide, polyimide, and any combinations thereof.

18. The medical device of claim 1 wherein the membrane is at least partially constructed of at least one material of the group consisting of: polyester, polyamide, polyethylene terephalate, crossliniked polyethylene, polyurethane, polyvinylchloride, polytetrafluoroethylene, nylon, polyether block amides, silicone, POC, polyether, and any combinations thereof.

19. The medical device of claim 1 wherein the stent is at least partially radiopaque.

20. The medical device of claim 1 wherein the stent is configured to be detectable by at least one of the following detection modalities: X-Ray, MRI, ultrasound, and any combination thereof.

21. The medical device of claim 1 wherein at least a portion of the stent comprises at least one therapeutic agent.

22. The medical device of claim 21 wherein the at least one therapeutic agent comprises a coating.

23. The medical device of claim 21 wherein the at least one therapeutic agent is selected from at least one member of the group consisting of: non-genetic therapeutic agents, genetic therapeutic agents, cellular material, and any combination thereof.

24. The medical device of claim 21 wherein the at least one therapeutic agent comprises at least one polymer agent.

25. The medical device of claim 1 wherein the catheter is a fixed-wire catheter.

26. The medical device of claim 1 wherein the catheter shaft defines a guidewire lumen for passage of a guidewire therethrough.

27. The medical device of claim 1 wherein the engagement region comprises a weld between the sheath and the rolling membrane.

28. The medical device of claim 1 wherein the engagement region comprises a chemical adhesive between the sheath and membrane.

* * * * *